US 9,743,847 B2

(12) United States Patent
Gloth et al.

(10) Patent No.: US 9,743,847 B2
(45) Date of Patent: Aug. 29, 2017

(54) BLOOD PRESSURE CUFF WITH TAPERED BLADDER

(71) Applicants: Sean Gloth, Clarksville, MD (US); Christopher Gloth, Clarksville, MD (US)

(72) Inventors: Sean Gloth, Clarksville, MD (US); Christopher Gloth, Clarksville, MD (US)

(73) Assignee: St. Luke Medical, Inc., Clarksville, MD (US)

( * ) Notice: Subject to any disclaimer, the term of this patent is extended or adjusted under 35 U.S.C. 154(b) by 742 days.

(21) Appl. No.: 13/837,095

(22) Filed: Mar. 15, 2013

(65) Prior Publication Data

US 2014/0276147 A1 Sep. 18, 2014

(51) Int. Cl.
*A61B 5/022* (2006.01)

(52) U.S. Cl.
CPC .................................. *A61B 5/02233* (2013.01)

(58) Field of Classification Search
CPC .......................... A61B 5/02233; A61B 17/135
See application file for complete search history.

(56) References Cited

U.S. PATENT DOCUMENTS

| 1,063,287 | A |   | 6/1913 | Rogers et al. |
|---|---|---|---|---|
| 2,841,149 | A |   | 7/1958 | Marsden |
| 3,504,675 | A | * | 4/1970 | Bishop, Jr. .................... 606/202 |
| 3,513,831 | A |   | 5/1970 | Hirsch |
| 3,669,096 | A |   | 6/1972 | Hurwitz |
| 3,699,945 | A |   | 10/1972 | Hanafin |
| 4,378,009 | A |   | 3/1983 | Rowley et al. |
| 4,542,743 | A |   | 9/1985 | Dunn et al. |
| 4,716,906 | A |   | 1/1988 | Ruff |
| 4,890,625 | A |   | 1/1990 | Sorensen |
| 4,901,732 | A |   | 2/1990 | Williams |
| 5,354,460 | A |   | 10/1994 | Kearney et al. |
| 5,660,182 | A |   | 8/1997 | Kuroshaki et al. |
| 5,871,499 | A |   | 2/1999 | Hahn et al. |
| 6,171,271 | B1 |   | 1/2001 | Hornberg |
| 6,245,023 | B1 |   | 6/2001 | Clemmons |
| 6,866,636 | B2 |   | 3/2005 | Inoue et al. |

(Continued)

OTHER PUBLICATIONS

Maxwell, George et al., "Comparison of the Conical Cuff and the Standard Rectangular Cuff", *International Journal of Epidemiology*, vol. 14, No. 3,(1985),468-472.

(Continued)

*Primary Examiner* — Patricia Mallari
*Assistant Examiner* — Michael Catina
(74) *Attorney, Agent, or Firm* — Pepper Hamilton LLP (57) ABSTRACT

A blood pressure cuff includes an alignment tab, a sleeve, and an inflatable bladder disposed within the sleeve. The inflatable bladder includes a first rectangular section having a first width, a second rectangular section having a second width, wherein the second width is larger than the first width, and a tapered section extending between the first rectangular section and the second rectangular section. The tapered section may be linearly tapered or a curved taper. A length from an edge of the alignment tab to the second end of the first rectangular section adjacent the tapered section is approximately equal to a minimum arm circumference for the blood pressure cuff.

10 Claims, 6 Drawing Sheets

(56) References Cited

U.S. PATENT DOCUMENTS

| | | |
|---|---|---|
| 7,427,268 B2 | 9/2008 | Millay et al. |
| 8,361,107 B2 | 1/2013 | Grabl |
| 2004/0034308 A1 | 2/2004 | Inoue et al. |
| 2004/0092833 A1 | 5/2004 | Just et al. |
| 2007/0135720 A1 | 6/2007 | Vinocur |
| 2009/0043215 A1* | 2/2009 | Grassl .......................... 600/499 |
| 2012/0130419 A1 | 5/2012 | Leschinsky |
| 2013/0109981 A1 | 5/2013 | Uesaka et al. |

OTHER PUBLICATIONS

Gotkin, Joel et al., "Dynasleeve—A Blood Pressure Cuff Suitable for Obese Patients", *Duke Diet and Fitness Center*, (Feb. 13, 2007).

International Search Report and Written Opinion dated Dec. 28, 2015 for PCT/US2015/50489.

European Search Report and Written Opinion dated Mar. 17, 2015 for EP 14184913.3.

Feder et al., Tapered Blood Pressure Cuff for Varying Arm Circumferences, The Fischell Department of Bioengineering (A. James Clark School of Engineering and University of Maryland), May 18, 2012, p. 1.

* cited by examiner

BLOOD PRESSURE CUFF WITH TAPERED BLADDER

FIELD OF THE INVENTION

This invention relates generally to blood pressure measurement, and more particularly to a blood pressure cuff (sphygmomanometer) that provides accurate measurements over a range of patient arm circumferences.

BACKGROUND

A patient's blood pressure is measured in almost all cases using a sphygmomanometer, or blood pressure cuff. This term refers to a device consisting of an inflatable bladder housed within a sleeve (cuff) and connected to a manometer. The cuff is wrapped around the patient's upper arm and the bladder inflated to restrict blood flow through the patient's brachial artery. The manometer is used to read the pressure at which the blood flow first resumes (known as the systolic blood pressure, or SBP) and the pressure at which the blood flow becomes unimpeded (known as the diastolic blood pressure, or DBP). These occurrences may be identified manually using a stethoscope (to listen for the appearance and disappearance of the Korotkoff sounds), or digitally using electronic calculation.

Currently, the typical blood pressure cuff is sized for a range of arm circumferences yet contains a bladder of fixed width. This is true despite the fact that the SBP and the DBP read by the manometer vary as the ratio of bladder width to arm circumference varies. As a result, any patient whose arm circumference does not fall at the center of the range corresponding to a given cuff size will receive an inaccurate blood pressure measurement. In an attempt to mitigate this problem, the American Heart Association (AHA) has recommended using seven different cuff sizes (corresponding to seven different ranges of arm circumference) for patients ranging from pediatric to large adult. Because each cuff size contains a fixed-width bladder, however, even using the appropriately sized cuff can result in up to a plus or minus 5% error in blood pressure readings. Furthermore, because following the AHA recommendation requires measuring the patient's arm before choosing the appropriate cuff size, many practitioners (for example in clinics, wards, and/or physicians' offices) ignore the recommendation and use a standard cuff with a 12-centimeter-wide bladder in almost all blood pressure measurements. This can result in even larger errors, on the order of 5-10 mm Hg in some tests, for both the SBP and the DBP. Such errors can lead to costly misdiagnoses, especially for patients whose blood pressures are near the cutoff levels for prescribing treatment for hypertension. Further, with cutoff levels used to prescribe hypertension medication, errors in blood pressure measurements that result in high blood pressure measurements may result in patients receiving medication who do not need the medication. This results in increased costs and patients being unnecessarily medicated. Errors in blood pressure measurements that result in low blood pressure measurements may result in patients that should receive blood pressure medication not receiving such medication, thereby resulting in health complications due to untreated hypertension.

It has been suggested that the ratio of the width of the bladder covering the artery to the patient's arm circumference should be approximately in the range of 40% in order to properly occlude the artery. In addition, it has been suggested that the bladder should encircle at least about 80% of the arm and less than 100% of the arm (such that the bladder does not overlap onto itself) in order to provide accurate readings. Based on the above discussion of current practices, there exists a need for a blood pressure cuff that meets both of these requirements for accuracy while fitting patients with a range of arm circumferences.

SUMMARY OF THE INVENTION

Embodiments hereof relate to a blood pressure cuff for accurately measuring blood pressure. In an embodiment, the blood pressure cuff includes an alignment tab having an edge, a sleeve, and an inflatable bladder disposed within the sleeve. The inflatable bladder includes a first rectangular section having a first width, a first end and a second end, and a tapered section of increasing width extending from the second end of the first rectangular section in a direction away from the alignment tab. The length from the edge of the alignment tab to the second end of the first rectangular section is approximately equal to a minimum arm circumference for the blood pressure cuff.

Embodiments hereof relate to a blood pressure cuff including a sleeve and an inflatable bladder disposed within the sleeve. The inflatable bladed includes a first rectangular section having a first width, a second rectangular section having a second width, wherein the second width is larger than the first width, and a tapered section extending between the first rectangular section and the second rectangular section. The tapered section may be linearly tapered or a curved taper.

DETAILED DESCRIPTION

Specific embodiments of the present invention are now described with reference to the figures, wherein like reference numbers indicate identical or functionally similar elements. Specific embodiments are now described with reference to the figures, wherein like reference numbers indicate identical or functionally similar elements.

The following detailed description is merely exemplary in nature and is not intended to limit the invention or the application and uses of the invention. Furthermore, there is no intention to be bound by any expressed or implied theory presented in the preceding technical field, background, brief summary or the following detailed description. The terms "sphygmomanometer" and "blood pressure cuff" are used throughout this specification interchangeably, and are understood by those of ordinary skill in the art as being interchangeable terms.

Figure 1:
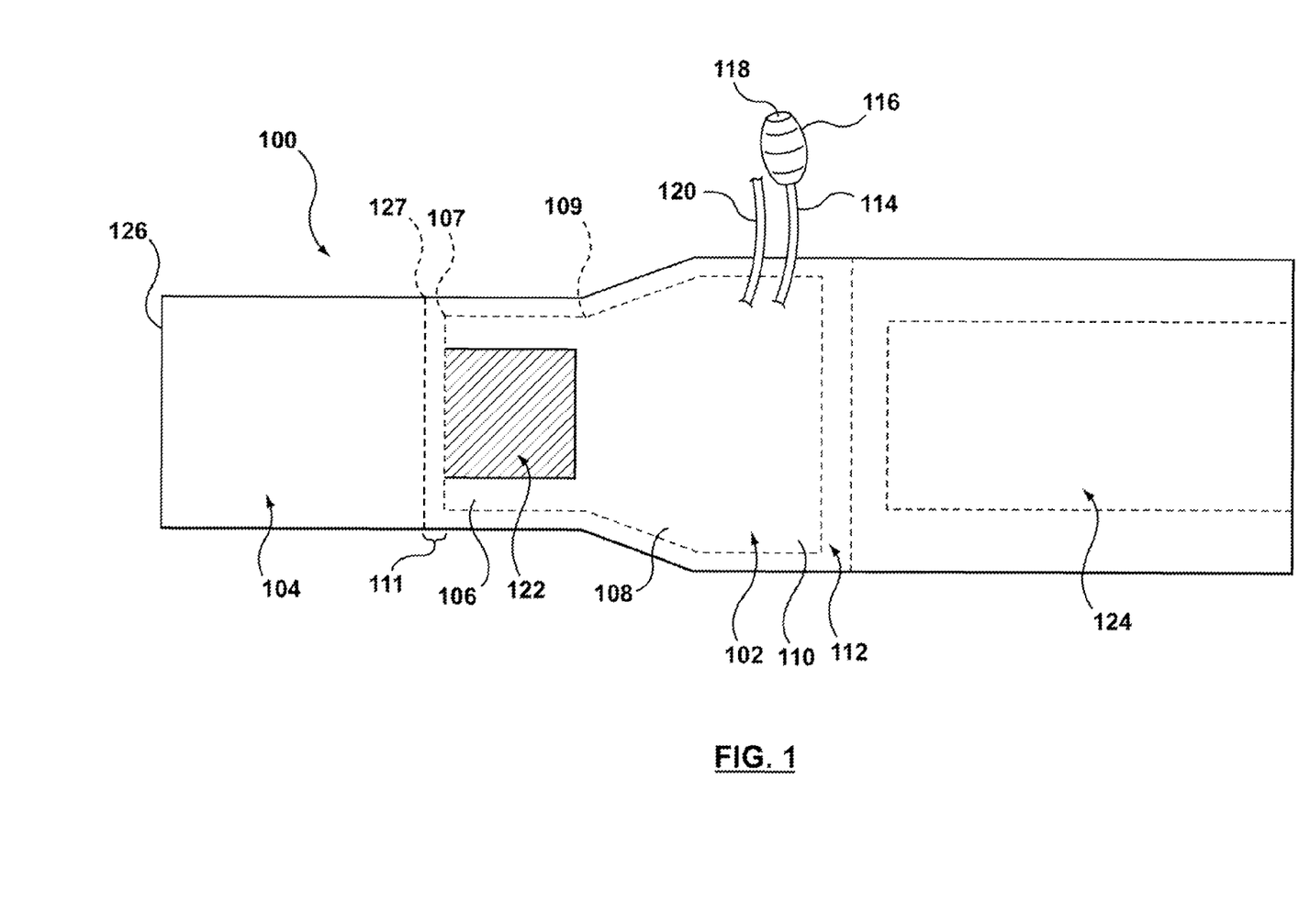
FIG. 1 is a schematic illustration of a blood pressure cuff with a linearly tapered bladder and an alignment tab.

FIG. 1 illustrates a schematic view of a blood pressure cuff 100 with a tapered bladder 102 and an alignment tab 104. Bladder 102 is inflatable and includes a narrow rectangular section 106, a linearly tapered section 108, and a wide rectangular section 110. Bladder 102 may be constructed of PVC rubber, plastic, or any other similar material that is generally non-permeable to air. Bladder 102 consists of two layers, which form a pocket for holding air. Bladder 102 is shown in FIG. 1 in dashed lines because it is housed within a sleeve 112. A tube 114 is connected at a first end to the internal pocket of bladder 102 and at a second end to a squeeze ball 116. An opening 118 in ball 116 allows atmospheric air to enter ball 116. When ball 116 is squeezed, air is transferred through tube 114 and into bladder 102 to inflate bladder 102. A second tube 120 has a first end connected to the internal pocket of bladder 102 and a second end (not shown) connected to a manometer (not shown).

In the embodiment of FIG. 1, hook and loop sections 122 and 124 on opposing sides of cuff 100 are used to secure cuff 100 around the patient's arm. However, other means of fixing the cuff to itself such that it remains in a fixed position once wrapped around the patient's arm may also be used. Additionally, while FIG. 1 shows the shape of sleeve 112 generally mimicking the shape of bladder 102, sleeve 112 may be of any shape larger than bladder 102 and may use seams or other means to ensure that bladder 102 does not move significantly within sleeve 112. Sleeve 112 may be constructed of nylon or similar fabric, or of any other sufficiently flexible material. Alignment tab 104 may be constructed of the same material as sleeve 112 or of a different sufficiently flexible material. While tab 104 is shown as generally rectangular in FIG. 1, it may be of any shape and it may be wider or narrower than sleeve 112 to which it is joined.

Figure 2:
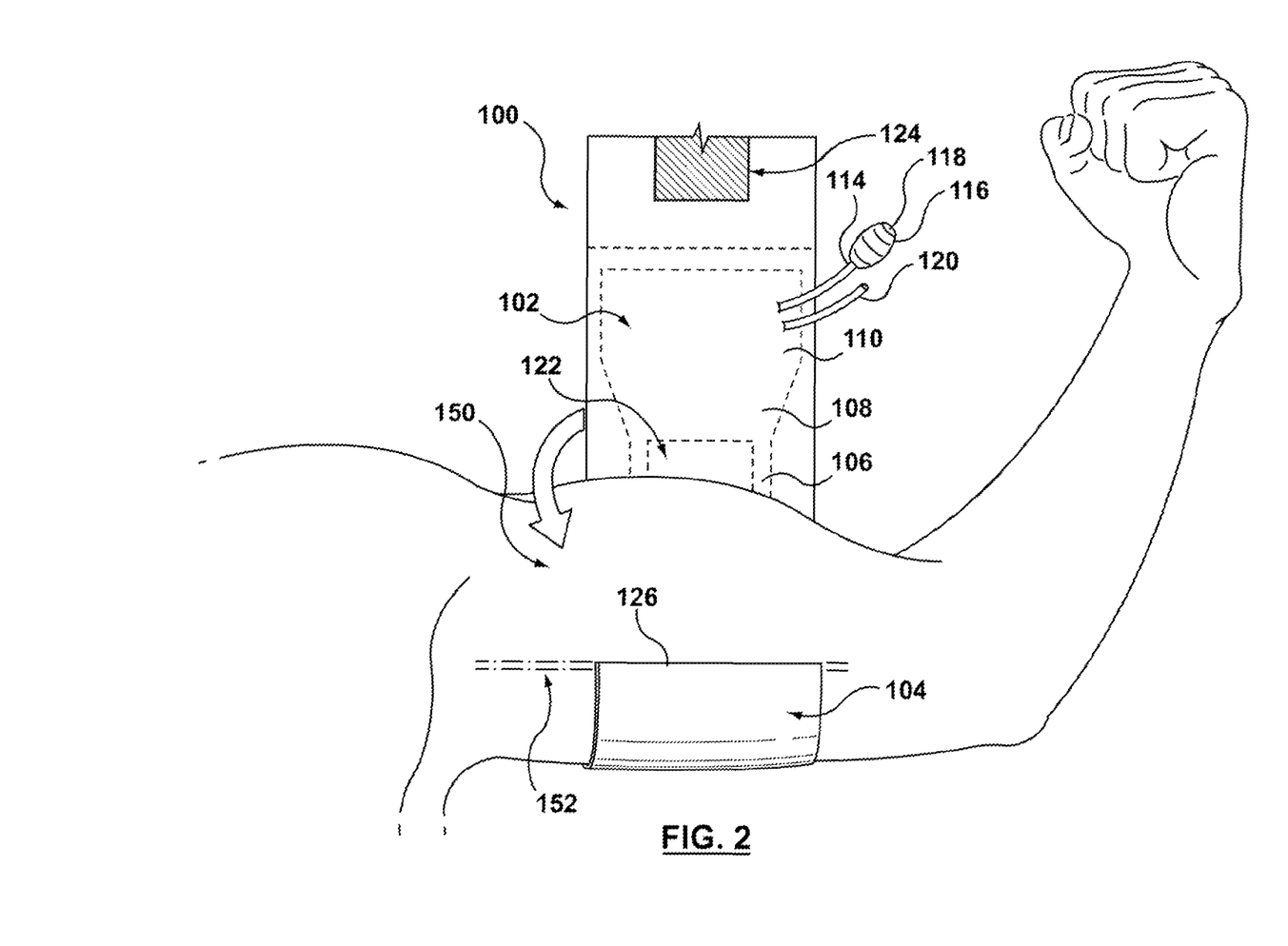
FIG. 2 is a schematic illustration of the method of aligning the blood pressure cuff on a patient's arm such that the bladder contacts the patient's brachial artery at the appropriate position for an accurate reading.

FIG. 2 schematically illustrates the method of aligning cuff 100 with the patient's arm 150. As shown in FIG. 2, an edge 126 of tab 104 is placed tangentially to the patient's brachial artery 152. Cuff 100 is wrapped around arm 150 such that bladder 102 intersects brachial artery 152, and then cuff 100 is fixed into position by attaching hook and loop sections 122 and 124 to each other. It is important that the method of aligning cuff 100 is easy so that users properly align cuff so that the proper width of bladder 102 is aligned with the brachial artery.

Alignment tab 104 is sized according to the range of arm circumferences for which cuff 100 is intended. The length of tab 104 that wraps around patient's arm 150 is such that narrow rectangular section 106 of bladder 102 intersects brachial artery 152 if the patient's arm circumference is equal to the minimum value supported by the particular size of cuff 100. Similarly, tab 104 ensures that wide rectangular section 110 intersects brachial artery 152 if the patient's arm circumference is equal to the maximum value supported by the cuff size, and that appropriate portion of linearly tapered section 108 intersects brachial artery 152 if the patient's arm circumference falls between the limits supported by the size of cuff 100. This design ensures that the ratio of bladder width (at the point where it intersects brachial artery 152) to arm circumference is maintained at the desired width of bladder to arm circumference ratios for any arm circumference falling within the range supported by the size of cuff 100. Additionally, the lengths of tab 104 and bladder 102 are such that, for an arm circumference falling within the bounds specified by the size of cuff 100, bladder 102 encircles the patient's arm 150 without overlapping onto itself.

Accordingly, as can be seen in the charts provided below, the length of tab 104 and the length of the narrow rectangular section 106 of bladder 102 add up to almost the minimum arm circumference for the cuff 100. The total is not equal to minimum arm circumference because there is a distance or gap 111 from a second end 127 of tab 104 to an edge 107 of the narrow rectangular section 106 of bladder 102 of approximately 1 cm. Accordingly, the length from edge 126 of tab 104 to a transition 109 from narrow rectangular section 106 of bladder 102 to tapered section 108 of bladder 108 is approximately equal to the minimum arm circumference for the cuff. Those skilled in the art would recognize that variations in the length of tab 104, narrow rectangular section 106, and gap 111 may be made provided that the total length from edge 126 of tab 104 to transition 109 is approximately the minimum circumference for the cuff. The term "approximately" or "Substantially" as used herein means "about" or "around" and is used to accommodate manufacturing tolerances and other minor variations. Accordingly, as used herein, the term "approximately" or "substantially" means within 5%. The table below provides exemplary sizes of parts of the cuff 100 for particular ranges of arm circumferences. The reference numerals used in the chart refer the FIG. 1, but the chart applies equally to the embodiment of FIG. 3, described below. All numbers provided within the table are in units of centimeters.

| Cuff Size | Arm Circ. Range | Tab 104 Length | Narr. Rect. 106 Length | Narr. Rect. 106 Width | Taper 108 Length | Wide Rect. 110 Length | Wide Rect. 110 Width |
| --- | --- | --- | --- | --- | --- | --- | --- |
| Small | 22-26 | 19 | 2 | 10.33 | 4 | 2 | 12.29 |
| Medium | 27-34 | 24 | 2 | 12.78 | 7 | 2 | 16.23 |
| Large | 35-44 | 32 | 2 | 16.73 | 9 | 2 | 21.18 |

Figure 4:
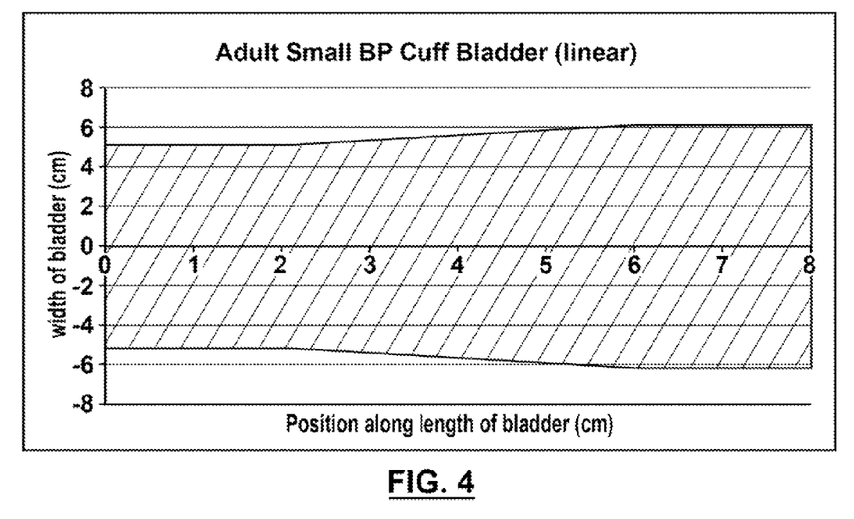
FIGS. 4-6 are graphs showing the width of a bladder in relation to a lengthwise distance from an edge of the bladder using a linear taper for each of a small, medium, and large cuff.
Figure 5:
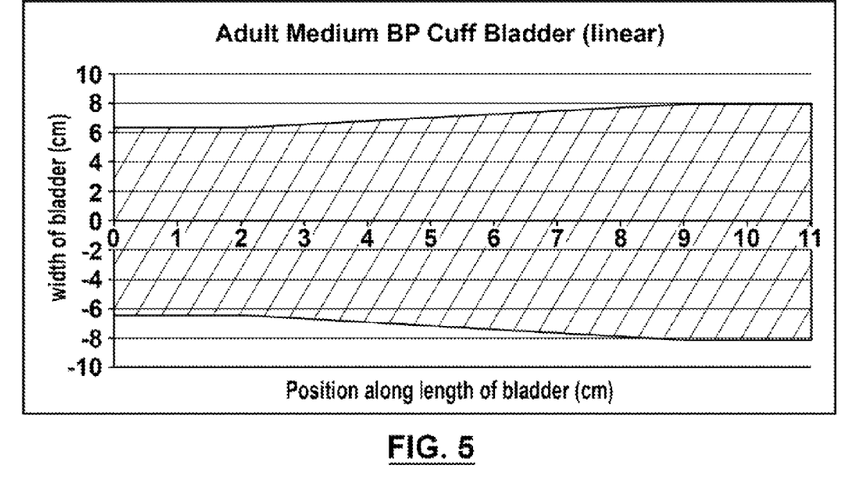
Figure 6:
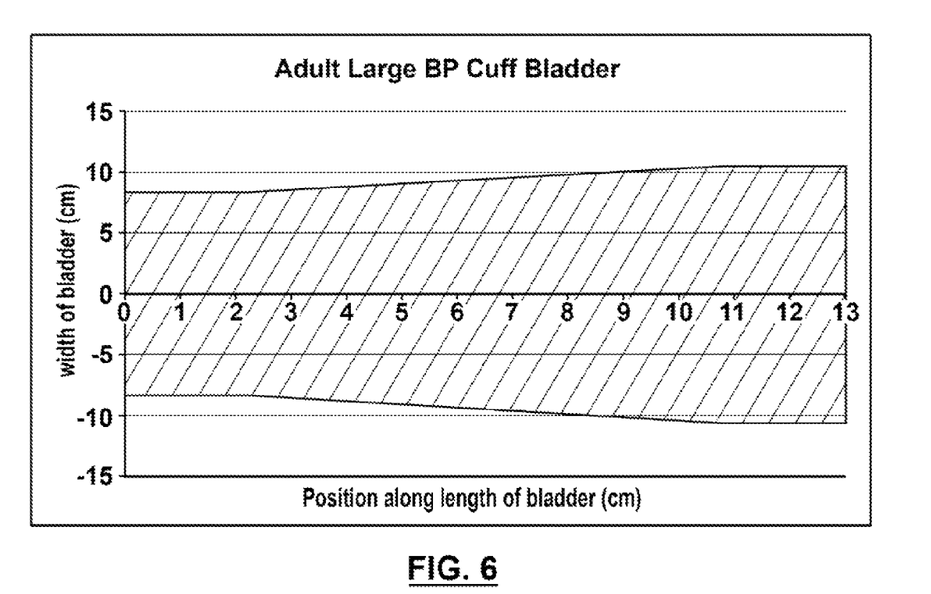

In the chart above, the taper is a linear taper. Thus, the width of the bladder along the taper length can be calculated by the commonly known formula for a line: $Y=m*X+b$, wherein m is equal to the slope and b is equal to the Y-axis intercept. In order to calculate the formula for the line of the tapered section, the bladder parameters may be laid out on a graph. Two points on the line can be determined by ½ the width of the bladder in the narrow section as the Y-axis at 2 cm along the X-axis and ½ the width of the wide section of the bladder as the Y-axis at 6 cm along the X-axis. One half of the width is used such that half of the bladder is above the X-axis and half of the bladder is below the X-axis. Solving the equation results in the line of the tapered section of the bladder of the small cuff identified above being defined as $Y=0.245*X+4.675$. FIGS. 4-6 show graphs of the bladder sections for small, medium, and adult cuffs with the dimensions as noted above. Further the width at the narrow rectangular section 106 and the width of the wide rectangular section 110 are each approximately calculated according to the formula: $W=(C-LOG(C))/2$; wherein C=the circumference of the patient's arm and W=the width of the tapered section for a particular circumference.

Figure 3:
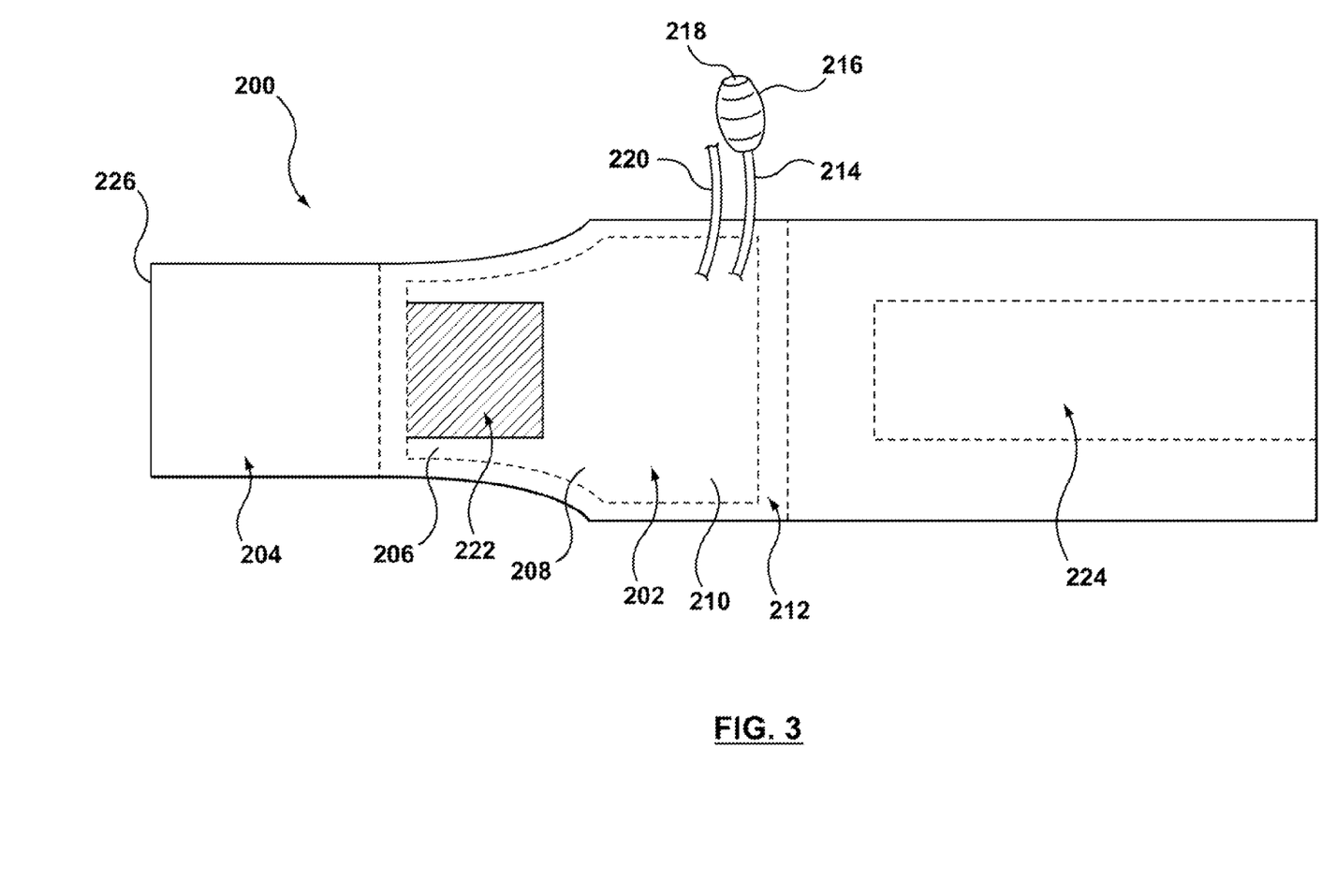
FIG. 3 is a schematic illustration of a blood pressure cuff with a curved tapered bladder and an alignment tab.
Figure 7:
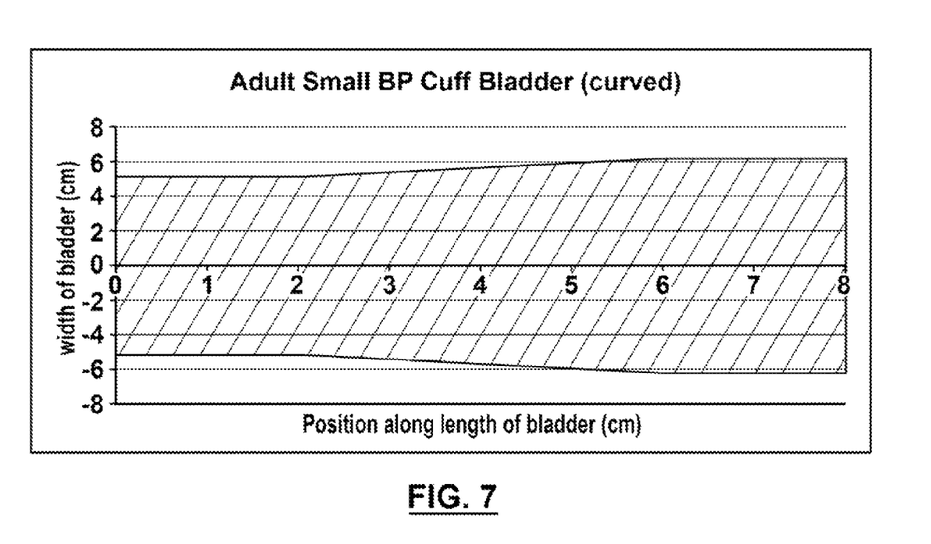
FIGS. 7-9 are graphs showing the width of a bladder in relation to a lengthwise distance from an edge of the bladder using a curved taper for each of a small, medium, and large cuff.
Figure 8:
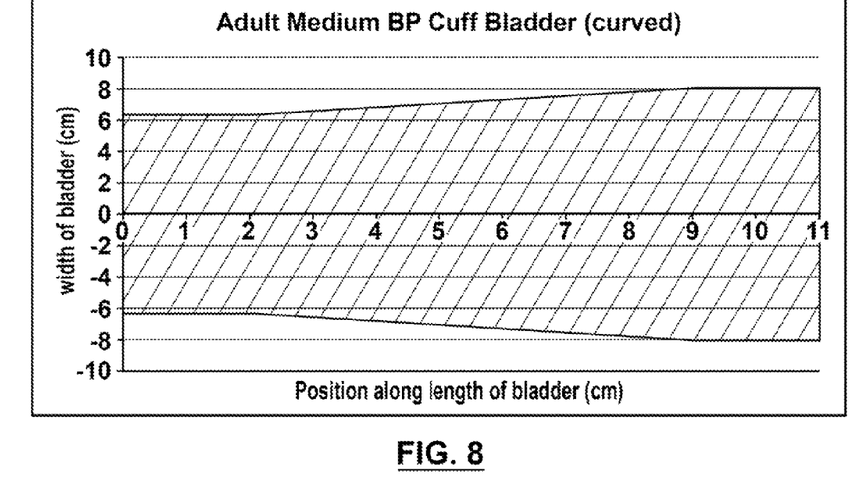
Figure 9:
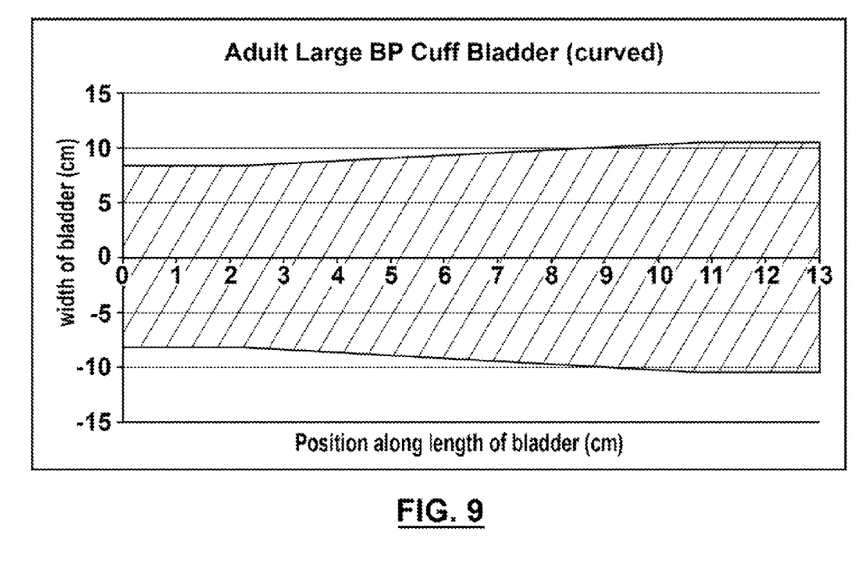

FIG. 3 illustrates a schematic view of another embodiment of a blood pressure cuff 200, which also contains an inflatable bladder 202 and an alignment tab 204. Cuff 200 of this embodiment is similar to cuff 100 except that bladder 202 includes a curved tapered section 208 between a narrow rectangular section 206 and a wide rectangular section 210. It has been found that a suitable curve is defined by the following formula: $W=(C-LOG(C))/2$; wherein C=the circumference of the patient's arm and W=the width of the tapered section for a particular circumference. Accordingly, whereas the chart above with the linear tapered section used the above formula for the width of the bladder at the narrow rectangular section and the wide rectangular section, the chart below uses the formula for each width. FIGS. 7-9 are graphs showing the bladder in accordance with the formula above. Otherwise, cuff 200 is similar to cuff 100. Bladder 202 is housed within a sleeve 212 and is inflatable via tube 214 and squeeze ball 216. A second tube 220 has a first end connected to the internal pocket of bladder 202 and a second end (not shown) connected to a manometer (not shown). The shapes and materials of bladder 202, tab 204, and sleeve 212 are as outlined above for the first embodiment. Additionally, FIG. 3 shows the inclusion of opposing hook and loop sections 222 and 224 on cuff 200, but any other means of securing cuff 200 to itself around a patient's arm may be used. Cuff 200 is aligned with the patient's arm in the same manner as is illustrated in FIG. 2 and discussed above.

Although specific embodiments of the linear taper and curved taper have been presented above, those skilled in the art would recognize that other linear tapers or curved tapers may be utilized. For example, in the linear taper embodiment described, the ratio of the width of the bladder covering the artery to the patient's arm circumference is approximately 47%. The design of the taper of the bladder may be modified to accommodate any desired ratio. For example, and not by way of limitation, a bladder of a blood pressure cuff may be designed to accommodate a 40% ratio using this following cuff and bladder dimensions (all in cm).

| Cuff Size | Arm Circ. | Tab Length | Distance from Narrow Bladder Edge | Bladder width |
|---|---|---|---|---|
| Small | 22 | 19 | 0 | 8.8 |
| Small | 22 | 19 | 1 | 8.8 |
| Small | 22 | 19 | 2 | 8.8 |
| Small | 23 | 19 | 3 | 9.2 |
| Small | 24 | 19 | 4 | 9.6 |
| Small | 25 | 19 | 5 | 10 |
| Small | 26 | 19 | 6 | 10.4 |
| Small | 26 | 19 | 7 | 10.4 |
| Small | 26 | 19 | 8 | 10.4 |
| Medium | 27 | 24 | 0 | 10.8 |
| Medium | 27 | 24 | 1 | 10.8 |
| Medium | 27 | 24 | 2 | 10.8 |
| Medium | 28 | 24 | 3 | 11.2 |
| Medium | 29 | 24 | 4 | 11.6 |
| Medium | 30 | 24 | 5 | 12.0 |
| Medium | 31 | 24 | 6 | 12.4 |
| Medium | 32 | 24 | 7 | 12.8 |
| Medium | 33 | 24 | 8 | 13.2 |
| Medium | 34 | 24 | 9 | 13.6 |
| Medium | 34 | 24 | 10 | 13.6 |
| Medium | 34 | 24 | 11 | 13.6 |
| Large | 35 | 32 | 0 | 14.0 |
| Large | 35 | 32 | 1 | 14.0 |
| Large | 35 | 32 | 2 | 14.0 |
| Large | 36 | 32 | 3 | 14.4 |
| Large | 37 | 32 | 4 | 14.8 |
| Large | 38 | 32 | 5 | 15.2 |
| Large | 39 | 32 | 6 | 15.6 |
| Large | 40 | 32 | 7 | 16.0 |
| Large | 41 | 32 | 8 | 16.4 |
| Large | 42 | 32 | 9 | 16.8 |
| Large | 43 | 32 | 10 | 17.2 |
| Large | 44 | 32 | 11 | 17.6 |
| Large | 44 | 32 | 12 | 17.6 |
| Large | 44 | 32 | 13 | 17.6 |

Those skilled in the art would recognize that variations in the desired ratio of bladder width to arm circumference, length of narrow rectangular section of the bladder, and length of the tab may be made such that the desired width of bladder corresponds to each arm circumference with the alignment method described above.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. A blood pressure cuff comprising:
   an alignment tab having an edge;
   a sleeve; and
   an inflatable bladder disposed within the sleeve, the inflatable bladder including a first rectangular section having a first width, a first end and a second end, and a tapered section of increasing width extending from the second end of the first rectangular section in a direction away from the alignment tab;
   wherein a length from the edge of the alignment tab to the second end of the first rectangular section is approximately equal to a minimum arm circumference for the blood pressure cuff;
   wherein the blood pressure cuff is sized for a range of arm circumferences, the range including a first circumference and a second circumference, wherein the second circumference is larger than the first circumference; and
   wherein the first width equals approximately one half the difference of the first circumference and the log of the first circumference ($W_1=(C_1-LOG(C_1))/2$).

2. The blood pressure cuff of claim 1, wherein the inflatable bladder further includes a second rectangular section having a second width larger than the first width, wherein the tapered section extends between the first rectangular section and the second rectangular section, wherein the second width equals approximately one half the difference of the second circumference and the log of the second circumference ($W_2=(C_2-LOG(C_2))/2$).

3. The blood pressure cuff of claim 1, wherein the tapered section comprises a linear taper.

4. The blood pressure cuff of claim 1, wherein the tapered section comprises a curved taper.

5. The blood pressure cuff of claim 1, wherein the blood pressure cuff is configured for arm circumferences between approximately 22 cm and 26 cm and the length from the edge of the alignment tab to the second end of the first rectangular section is approximately 22 cm.

6. The blood pressure cuff of claim 1, wherein the blood pressure cuff is configured for arm circumferences between approximately 27 cm and 34 cm and the length from the edge of the alignment tab to the second end of the first rectangular section is approximately 27 cm.

7. The blood pressure cuff of claim 1, wherein the blood pressure cuff is configured for arm circumferences between approximately 35 cm and 44 cm and the length from the edge of the alignment tab to the second end of the first rectangular section is approximately 35 cm.

8. A blood pressure cuff comprising:
a sleeve; and
an inflatable bladder disposed within the sleeve, wherein the bladder includes a first rectangular section having a first width, a second rectangular section having a second width, wherein the second width is larger than the first width, and a tapered section extending between the first rectangular section and the second rectangular section;
wherein the blood pressure cuff is sized for a range of arm circumferences including a first circumference and a second circumference, wherein the second circumference is larger than the first circumference;
wherein the first width equals approximately one half the difference of the first circumference and the log of the first circumference ($W_1=(C_1-LOG(C_1))/2$); and
wherein the second width equals approximately one half the difference of the second circumference and the log of the second circumference ($W_2=(C_2-LOG(C_2))/2$).

9. The blood pressure cuff of claim 8, wherein the tapered section comprises a linear taper.

10. The blood pressure cuff of claim 8, wherein the tapered section comprises a curved taper.

\* \* \* \* \*